(12) United States Patent
Bertz et al.

(10) Patent No.: US 7,208,143 B2
(45) Date of Patent: *Apr. 24, 2007

(54) ANTIPERSPIRANT COMPOSITIONS

(75) Inventors: Steven H. Bertz, Morristown, NJ (US); Steven A. Orofino, Hamburg, NJ (US); Blanca Gomez, Newark, NJ (US)

(73) Assignee: ISP Investments Inc., Wilmington, DE (US)

( * ) Notice: Subject to any disclaimer, the term of this patent is extended or adjusted under 35 U.S.C. 154(b) by 110 days.

This patent is subject to a terminal disclaimer.

(21) Appl. No.: 10/952,949

(22) Filed: Sep. 29, 2004

(65) Prior Publication Data

US 2006/0067901 A1    Mar. 30, 2006

(51) Int. Cl.
*A61Q 15/00* (2006.01)
*A61K 8/02* (2006.01)
*A61K 8/06* (2006.01)

(52) U.S. Cl. .............. 424/65; 424/66; 424/68; 424/400; 424/401; 514/937; 514/938

(58) Field of Classification Search .......... 424/65, 424/66, 68, 400, 401; 514/937, 938
See application file for complete search history.

(56) References Cited

U.S. PATENT DOCUMENTS

| 5,500,209 | A | * | 3/1996 | Mendolia et al. ............. 424/66 |
| 5,510,120 | A | * | 4/1996 | Jones et al. ................. 424/499 |
| 5,833,999 | A | * | 11/1998 | Trinh et al. ................. 424/401 |
| 6,589,921 | B2 | * | 7/2003 | Herrmann et al. .......... 510/102 |
| 6,593,476 | B2 | * | 7/2003 | Heywang et al. ......... 548/310.7 |
| 2005/0288205 | A1 | * | 12/2005 | Walele et al. ............... 510/392 |

FOREIGN PATENT DOCUMENTS

| JP | 2003137758 | * | 10/2001 |
| WO | WO 9323364 | * | 5/1993 |

* cited by examiner

*Primary Examiner*—Shelley A. Dodson
(74) *Attorney, Agent, or Firm*—William J. Davis; Walter Katz

(57) ABSTRACT

What is described herein is an antiperspirant composition including an active antiperspirant ingredient, and a phenylethyl, benzyl or substituted benzyl ester as additive therein, which is an aryl carboxylic ester of 2-phenylethyl alcohol, 1-phenylethyl alcohol or benzyl alcohol, which leaves a reduced visible white chalky residue on the skin of the user.

9 Claims, No Drawings

ANTIPERSPIRANT COMPOSITIONS

STATEMENT OF RELATED APPLICATIONS

The present application is related to co-pending U.S. application Ser. No. 10/859,533; filed Jun. 2, 2004, which is a continuation-in-part of co-pending U.S. application Ser. No. 10/617,497; filed Jul. 11, 2003, the disclosures of which are hereby incorporated by reference in their entirety.

BACKGROUND OF THE INVENTION

1. Field of the Invention

This invention relates to antiperspirant compositions, and more particularly, to new and improved antiperspirant compositions which leave a reduced visible residue on the skin of the user.

2. Description of the Prior Art

Antiperspirant compositions are well known in the art. See, e.g., U.S. Pat. Nos. 4,985,238; 5,302,381; 5,376,362; 5,417,963; 5,482,702; and 5,486,355. The active antiperspirant ingredient in such compositions usually is an inorganic compound, e.g., an aluminum, zirconium, or zinc salt such as an aluminum zirconium tetrachlorohydrate complex with glycine.

Many solid antiperspirant compositions have been described in the chemical and cosmetic literature. These compositions generally tend to fall into one of two classes: emulsion sticks and suspensoid sticks. Emulsion sticks contain a solution of the antiperspirant active incorporated into the stick via an emulsion. Although emulsion sticks may be desirable in certain respects, they tend to be unstable, have poor aesthetics (e.g., are overly hard, greasy or sticky), and leave a visible residue on the skin after use. Suspensoid sticks contain the powdered antiperspirant active suspended in the stick without the use of water or an emulsion. While suspensoids tend to be stable, they may be brittle and hard and, more importantly, they tend to leave an unsightly white chalky residue on the skin after application. This residue is not only aesthetically displeasing to the user, but can also discolor clothing. It has now been discovered that when a phenylethyl or benzyl ester is incorporated into water-free suspensoid antiperspirant stick compositions, they exhibit excellent antiperspirant efficacy and aesthetics, while leaving reduced visible residue on the skin of the user.

Accordingly, it is an object of this invention to provide an antiperspirant composition which leaves a reduced visible residue on the skin of the user.

Another object of the invention is to provide an antiperspirant composition containing an additive preferably having a refractive index which substantially matches the refractive index of the white, chalky residue formed after use thereby significantly reducing the appearance of the visible white, chalky residue on the skin of the user.

Still another object of this invention is to provide an antiperspirant composition which includes an active antiperspirant ingredient and a phenylethyl, benzyl or substituted benzyl ester as additive therein, which is an aryl carboxylic ester of 2-phenylethyl alcohol, 1-phenylethyl alcohol or benzyl alcohol, preferably having a refractive index which substantially matches the refractive index of the white, chalky residue thereby reducing the visible white appearance of the residue.

These and other objects and features of the invention will be made apparent from the following description thereof.

SUMMARY OF THE INVENTION

What is described herein is an antiperspirant composition including
(a) an active antiperspirant ingredient, and
(b) a phenylethyl, benzyl or substituted benzyl ester as additive therein, which is an aryl carboxylic ester of 2-phenylethyl alcohol, 1-phenylethyl alcohol or benzyl alcohol, which leaves a reduced visible white chalky residue on the skin of the user.

Representative phenylethyl esters include 2-phenylethyl benzoate, 2-phenethyl toluate or di-2-phenylethyl phthalate, 1-phenylethyl benzoate, or benzyl benzoate, preferably 2-phenylethyl benzoate.

The antiperspirant composition of the invention may take the form of an antiperspirant stick, lotion, cream, roll-on, solution or aerosol.

Suitable active antiperspirant ingredients include inorganic salt or organic compound, preferably an aluminum, zirconium or zinc salt, or mixtures thereof.

Most preferably, the antiperspirant ingredient is a coordination complex of aluminum zirconium tetrachlorohydrate and glycine.

As a feature of the invention, the refractive index of (b) in the composition herein substantially matches the refractive index of the white, chalky residue formed after use of the antiperspirant, thereby reducing the visible white, chalky residue which may form on the skin of the user.

The refractive index value of the phenylethyl or benzyl ester is about 1.5, which substantially matches that of the white residue.

DETAILED DESCRIPTION OF THE INVENTION

In accordance with the invention, it has been discovered herein that an antiperspirant composition which includes a phenethyl aryl ester as additive can mask the whitening effect of the unsightly white, chalky residue formed after use of the composition. Accordingly, the user experiences a reduced visible or non-whitening residue on the skin which is aesthetically pleasing to the consumer.

The phenethyl ester used as additive in the antiperspirant compositions of the invention is described in detail in the aforementioned patent applications as an aryl carboxylic ester of phenylethyl alcohol, e.g., 2-phenylethyl benzoate (X-TEND™ 226, ISP), 2-phenylethyl toluate or di-2-phenylethyl phthalate. These compounds have a relatively high refractive index of about 1.5 which substantially matches the refractive index of the white, chalky residue. This refractive index matching manifests itself in a light effect on the residue so that effectively the user does not see any white residue.

While the invention will be described herein with particular emphasis on antiperspirant stick compositions, it will be understood that lotions, creams, roll-on solutions and aerosols may be used as well.

Typically, antiperspirant stick compositions include (a) an antiperspirant active ingredient, (b) a volatile silicone oil; (c) a water-insoluble emollient; (d) a low melting wax; (e) a coupling agent; and (f) a surface active agent.

The 2-phenylethyl benzoate, toluate or phthalate was prepared by heating a mixture of 2-phenylethyl alcohol and the aryl carboxylic acid with a tin catalyst, and recovering the product. This process is described in detail in the above-related co-pending U.S. patent applications, the entire contents of which are incorporated by reference herein. The product is a free-flowing, clear, substantially colorless liquid with a density of about 1.09.

Suitably, the phenethyl or benzyl ester additive is employed in the antiperspirant composition of the invention in an amount of about 1 to 10% by wt. of the composition, preferably about 2 to 7 wt. %.

The invention will now be described with reference to the following examples, in which:

Example 1 below shows a typical antiperspirant stick composition with aluminum zirconium tetrachlorohydrex GLY using 2-phenylethyl benzoate as anti-whitening agent therein.

The antiperspirant sticks of the invention were prepared by first combining the ingredients listed in Phase A while mixing and heating to 75–80° C. Cooling was begun and Phase B was added in the order listed while mixing well between additions. Then Phase C was added and mixing continued. The resultant composition was poured into suitable stick containers at 50–53° C. and solidified.

EXAMPLE 1

Antiperspirant Stick with 2-Phenylethyl Benzoate and Zirconium Salt

| Ingredients | % w/w |
| --- | --- |
| Phase A | |
| SI-TEC ™ CM 040 | 42.00 |
| Paraffin | 6.50 |
| Stearyl Alcohol | 15.00 |
| X-TEND ™ 226 | 5.00 |
| Phase B | |
| Zirconium Salt | 25.00 |
| Talc | 5.75 |
| Phase C | |
| CK-1 Fragrance | 0.75 |
| Total | 100.00% |

EXAMPLE 2

Antiperspirant Stick with 2-Phenylethyl Benzoate and Aluminum Chlorohydrate

| Ingredients | % w/w |
| --- | --- |
| Phase A | |
| SI-TEC ™ CM 040 | 42.00 |
| Paraffins | 6.50 |
| Stearyl Alcohol | 15.00 |
| X-TEND ™ 226 | 5.00 |
| Phase B | |
| Aluminum Chlorohydrate | 25.00 |
| Talc | 5.75 |
| Phase C | |
| CK-1 Fragrance | 0.75 |
| Total | 100.00% |

EXAMPLE 3

Control-1

Antiperspirant Stick Without 2-Phenylethyl Benzoate with Zirconium Salt

| Ingredients | % w/w |
| --- | --- |
| Phase A | |
| SI-TEC ™ CM 040 | 47.00 |
| Paraffins | 6.50 |
| Stearyl Alcohol | 15.00 |
| Phase B | |
| Zirconium Salt | 25.00 |
| Talc | 5.75 |
| Phase C | |
| CK-1 Fragrance | 0.75 |
| Total | 100.00% |

EXAMPLE 4

Control-2

Antiperspirant Stick Without 2-Phenylethyl Benzoate with Aluminum Chlorohydrate Salt

| Ingredients | % w/w |
| --- | --- |
| Phase A | |
| SI-TEC ™ CM 040 | 47.00 |
| Paraffins | 6.50 |
| Stearyl Alcohol | 15.00 |
| Phase B | |
| Aluminum Chlorohydrate | 25.00 |
| Talc | 5.75 |
| Phase C | |
| CK-1 Fragrance | 0.75 |
| Total | 100.00% |

The efficacy of the antiperspirant stick composition of the invention as an anti-whitening product was determined by visually assessing the residue produced after swiping onto a black card. The results show that the antiperspirant stick of the present invention (Examples 1–2) substantially reduced the observable white residue as compared to the control sticks (Examples 3–4), without the invention ingredient.

While the invention has been described with particular reference to certain embodiments thereof, it will be understood that changes and modifications may be made which are within the skill of the art. Accordingly, it is intended to be bound only by the following claims, in which.

What is claimed is:

1. An antiperspirant composition comprising
   (a) an active antiperspirant ingredient, and
   (b) an aryl carboxylic ester of 2-phenylethyl alcohol, as additive therein, which leaves a reduced visible white chalky residue on the skin of the user.

2. A composition according to claim 1 wherein said phenylethyl ester is 2-phenylethyl benzoate.

3. A composition according to claim 1 in the form of an antiperspirant stick, lotion, cream, roll-on, solution or aerosol.

4. A composition according to claim 1 wherein said active antiperspirant ingredient is an inorganic salt or organic compound.

5. A composition according to claim 4 wherein said inorganic salt or organic compound is an aluminum, zirconium or zinc salt, or mixtures thereof.

6. A composition according to claim 5 wherein said antiperspirant ingredient is a coordination complex of aluminum zirconium tetrachlorohydrate and glycine.

7. A composition according to claim 5 wherein said inorganic compound is aluminum chlorohydrate.

8. A composition according to claim 1 wherein the refractive index of (b) therein substantially matches the refractive index of the white, chalky residue formed after use thereby reducing the visible white, chalky residue on the skin of the user.

9. A composition according to claim 8 wherein the refractive index value of said 2-phenylethyl benzoate is about 1.5.

* * * * *